United States Patent
Shah et al.

(10) Patent No.: US 10,307,603 B2
(45) Date of Patent: Jun. 4, 2019

(54) HERMETIC PACKAGE WITH INDUCTORS AND CAPACITORS INTEGRATED INTO CERAMIC HOUSING

(71) Applicant: Verily Life Sciences LLC, Mountain View, CA (US)

(72) Inventors: Kedar Shah, Burlingame, CA (US); Peng Cong, San Francisco, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 37 days.

(21) Appl. No.: 15/725,866

(22) Filed: Oct. 5, 2017

(65) Prior Publication Data

US 2018/0133487 A1  May 17, 2018

Related U.S. Application Data

(60) Provisional application No. 62/421,703, filed on Nov. 14, 2016.

(51) Int. Cl.

| | | |
|---|---|---|
| A61N 1/37 | (2006.01) | |
| A61N 1/375 | (2006.01) | |
| A61N 1/372 | (2006.01) | |
| A61N 1/378 | (2006.01) | |
| A61N 1/36 | (2006.01) | |
| A61N 1/05 | (2006.01) | |

(52) U.S. Cl.
CPC ......... *A61N 1/3754* (2013.01); *A61N 1/3756* (2013.01); *A61N 1/3787* (2013.01); *A61N 1/37205* (2013.01); *A61N 1/37223* (2013.01); *A61N 1/37229* (2013.01); *A61N 1/0534* (2013.01); *A61N 1/36038* (2017.08); *A61N 1/3758* (2013.01); *A61N 1/37512* (2017.08); *A61N 1/37514* (2017.08)

(58) Field of Classification Search
CPC combination set(s) only.
See application file for complete search history.

(56) References Cited

U.S. PATENT DOCUMENTS

| | | | |
|---|---|---|---|
| 5,019,829 A | 5/1991 | Heckman et al. | |
| 5,218,373 A | * 6/1993 | Heckaman | H01Q 1/405 333/246 |
| 5,312,439 A | 5/1994 | Loeb | |

(Continued)

FOREIGN PATENT DOCUMENTS

WO  98/37926 A1  9/1998

OTHER PUBLICATIONS

PCT/US2017/055796—International Search Report and Written Opinion of the International Searching Authority, dated Jan. 10, 2018, 13 pages.

*Primary Examiner* — Christopher Koharski
*Assistant Examiner* — Natasha Patel
(74) *Attorney, Agent, or Firm* — Christensen O'Connor Johnson Kindness PLLC

(57) ABSTRACT

An implantable device includes a cylindrical housing, a metallic feedthrough, a metallic collar, and a battery. The cylindrical housing has a sidewall and an internal cavity, and is formed from a ceramic. One or more electrical components are integrated into the sidewall. The metallic feedthrough is joined to a first end of the cylindrical housing. The metallic collar is joined to a second end of the cylindrical housing. The battery is joined to the metallic collar.

22 Claims, 5 Drawing Sheets

(56) References Cited

U.S. PATENT DOCUMENTS

| | | | |
|---|---|---|---|
| 6,415,184 B1 * | 7/2002 | Ishikawa | A61N 1/3605 607/116 |
| 7,518,553 B2 | 4/2009 | Zhang et al. | |
| 8,988,296 B2 | 3/2015 | Koskiniemi et al. | |
| 2004/0059392 A1 * | 3/2004 | Parramon | A61N 1/3605 607/36 |
| 2006/0247712 A1 * | 11/2006 | Fuller | A61N 1/37229 607/32 |
| 2006/0271109 A1 | 11/2006 | Kuzma et al. | |
| 2009/0163981 A1 * | 6/2009 | Stevenson | A61N 1/025 607/63 |
| 2009/0192381 A1 * | 7/2009 | Brockway | A61N 1/0504 600/373 |
| 2010/0168818 A1 * | 7/2010 | Barror | A61N 1/025 607/60 |

\* cited by examiner

HERMETIC PACKAGE WITH INDUCTORS AND CAPACITORS INTEGRATED INTO CERAMIC HOUSING

CROSS-REFERENCE TO RELATED APPLICATIONS

This application claims the benefit of U.S. Provisional Application No. 62/421,703, filed Nov. 14, 2016, which is incorporated by reference in its entirety.

TECHNICAL FIELD

This disclosure relates generally to implantable devices, and in particular but not exclusively, relates to integration of passive electronic elements in a hermetic package.

BACKGROUND INFORMATION

Implantable medical devices may typically include one or more power sources, electronics, and components for wireless connectivity to analytical devices located outside of a body. The implantable medical devices may generally be encased in bulky biocompatible packages that hermetically seal the internal electronics from the bodily fluid. Due to the bulk of the devices, miniaturization is desired, and driven for various reasons. One of these reasons may be related to the implant procedure. While the bulky devices may conventionally require invasive surgery, less invasive implant procedures would be possible with miniaturized implantable devices. While reduction in electronics and power supplies provide some reduction in size, the components that provide the wireless connectivity may provide a parallel path to miniaturization.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

DETAILED DESCRIPTION

Embodiments of a system and method for integrating inductors and/or capacitors into a ceramic housing are described herein. In the following description, numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Figure 1:
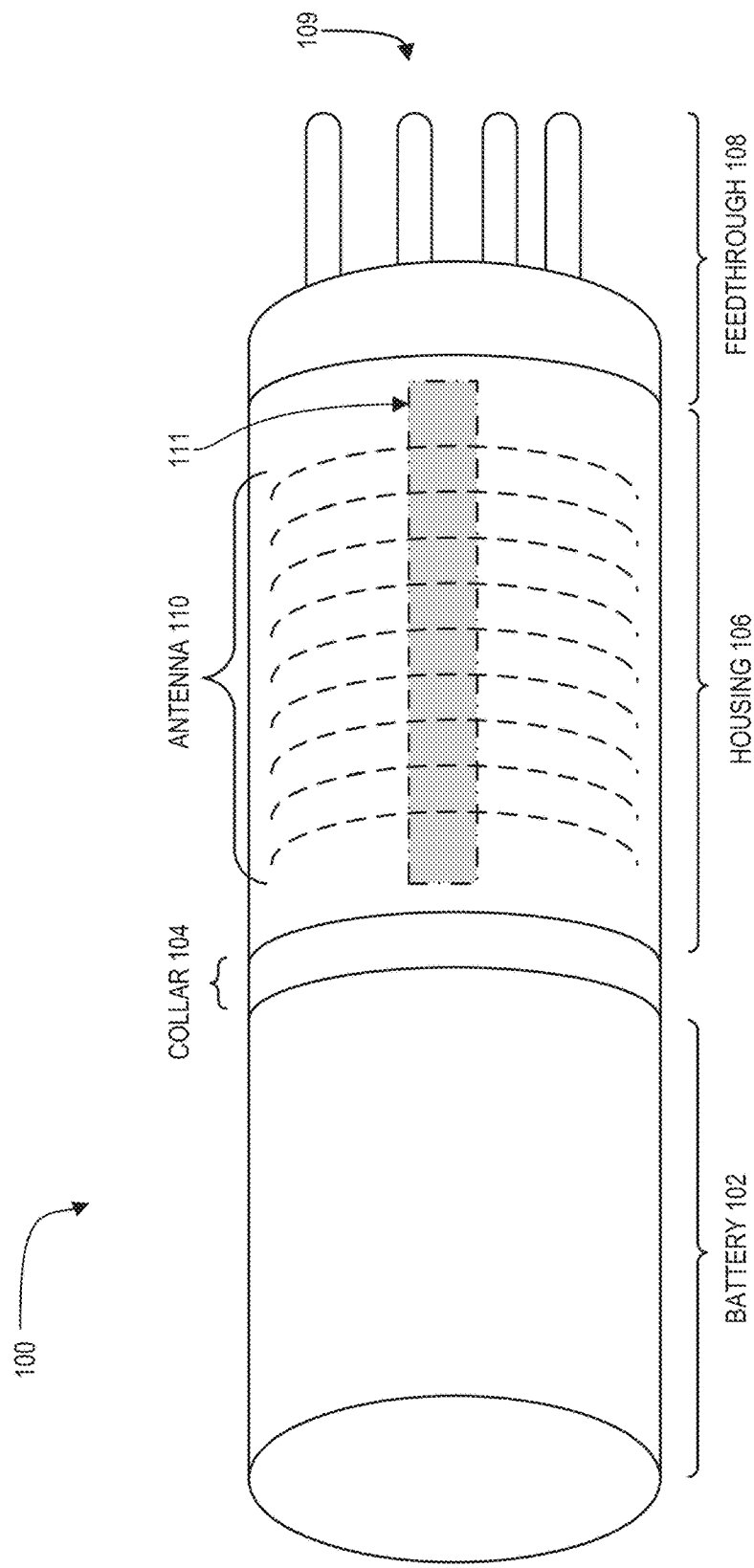
FIG. 1 is an implantable device including an integrated antenna in accordance with an embodiment of the present disclosure.

FIG. 1 is an implantable device 100 including an integrated antenna in accordance with an embodiment of the present disclosure. The implantable device 100 may be an active, implantable device that includes an antenna for power and/or data telemetry. Example devices may be pacemakers, cochlear implants, and neuro-stimulation implants, which may be permanently implanted into a patient, such as a human or an animal. Additionally, the implantable device 100 may provide a hermetic seal to protect any electronics internal to the device.

The illustrated embodiment of the implantable device 100 includes a battery 102, a collar 104, a housing 106, a feedthrough 108, an antenna 110, and circuitry 111. In some embodiments, the implantable device 100 may have a cylindrical shape. The implantable device 100 may in general include passive electronic components integrated into, e.g., imbedded into, a ceramic material forming at least the housing 106. Example passive electronics include inductive coils, e.g., the antenna 110, and capacitors (not shown). Integration of the passive electronic components may allow the implantable device 100 to be reduced in size, at least with respect to a diameter. In some embodiments, it may be desirable to reduce the diameter so that the implantable device 100 may be implanted via a needle or a trocar. For example, it may be desirable to have a diameter less than 1.5 cm. While a length of the implantable device 100 may also impact the invasiveness of the implant procedure, the length may have less impact than the diameter, and may be constrained by the function of the implantable device 100.

The battery 102 may provide power to electronics of the implantable device 100. For example, the battery 102 may provide power to circuitry 111 and any electrodes coupled via the feedthrough 108. In some embodiments, the battery 102 may be a rechargeable battery, and may be a liquid chemistry based battery. Example batteries may include lithium-ion, lithium polymer, nickel cadmium, nickel-metal hydride, and the like. The external surfaces of the battery 102 may be formed from or coated with biocompatible metallic materials. For example, the external surfaces of the battery 102 may be titanium. Additionally, the materials forming at least the outer surfaces of the battery 102 may be hermetic to prevent the seepage of fluid into the battery 102. For example, it may be desirable for the implantable device 102 to be hermetic so that bodily fluid does not leak into the implantable device 100 when implanted into a body, such as a human or animal body.

The collar 104 may be a metallic ring that adapts the battery to the housing 106. The metallic ring, which may be optional, may be included to reduce temperature stresses on the battery 102 that may occur when the battery 102 is joined to the housing 106. Like the external surface of the battery 102, external surfaces of the collar 104 may also be formed from or coated with one or more biocompatible metallic materials, such as titanium.

The feedthrough 108 may provide access to the circuitry 111 via one or more connectors 109. The one or more connectors 109 may provide an electrically conductive coupling between an external component, for example, to the circuit 111. For example, an electrode implanted into surrounding tissue may be coupled to one or more of the connectors 109 via a cable/wire so that the circuitry 111 may periodically provide charge to the electrode. Additionally, external surfaces of the feedthrough 108 may at least be coated with a biocompatible metallic material. Alternatively, a second collar 104 may be disposed between the housing 106 and the feedthrough 108.

The circuitry 111 may be disposed in an internal cavity of the housing 106 and may provide control electronics for implantable device 100. The circuitry 111 may at least be electrically coupled to the battery 102 and the antenna 112. While not shown, the circuitry 111 may additionally be coupled to one or more electrodes via the feedthrough 108. The circuitry 111 may be powered by the battery 102 and may further charge the battery 102 based on inductive coupling techniques using the antenna 110. The antenna 110 may also be used for data telemetry by the circuitry 111. In some embodiments, the circuitry 111 may include one or more integrated circuitry disposed on one or more substrates, such as printed circuit boards (PCBs).

The housing 106 may provide a biocompatible and hermetic enclosure for the circuitry 111. In some embodiments, the housing 106 may be cylindrically shaped with an internal cavity sized to accept the circuitry 111. In some embodiments, the housing 106 may be formed from one or more ceramics, which may be biocompatible and provide a hermetic enclosure to the circuitry 111. Example ceramics may include alumina, zirconium oxide, hydroxyapatite (HAP), and the like. By forming the housing 106 from a ceramic, electromagnetic signals may be able to penetrate the housing 106 so that the antenna 110 may transmit and receive such signals.

Additionally, the housing 106 may be shell-shaped with an annular wall having an inner diameter and an outer diameter, with a difference between the inner and outer diameter providing a finite sidewall thickness. The finite sidewall thickness may provide a volume for the integration of the antenna 110 into the housing 106. The antenna 110 may be accessible from within the housing 106 via one or more vias formed into an inner sidewall of the housing 106. For example, the one or more vias may provide entry and exit points for the antenna 110, and may allow for the circuitry 111 to be electrically coupled to the antenna 110. While only an inductor, e.g., the antenna 110, is shown in FIG. 1, other passive elements may also be integrated into the housing 106, such as a filtering capacitor.

The antenna 110 may be an inductor integrated into the housing 106. The antenna 110 may provide a means for data telemetry and inductive charging of the battery 102. The antenna may be formed form one or more metals imbedded into the housing 106. For example, the antenna 110 may be formed from platinum or gold integrated into the housing 106.

The implantable device 100 may be formed in one or more steps. For example, the feedthrough 108 and the collar 104 may be joined to the housing 106 using a brazing or a diffusion bonding method. Subsequently, the battery 102 may be joined to the collar 104 using laser welding, for example. Laser welding may be used because the elevated temperatures generated during the welding process may be localized to the battery 102/collar 104 interface, which may reduce the affect the elevated temperatures may have on the battery 102.

Figure 2:
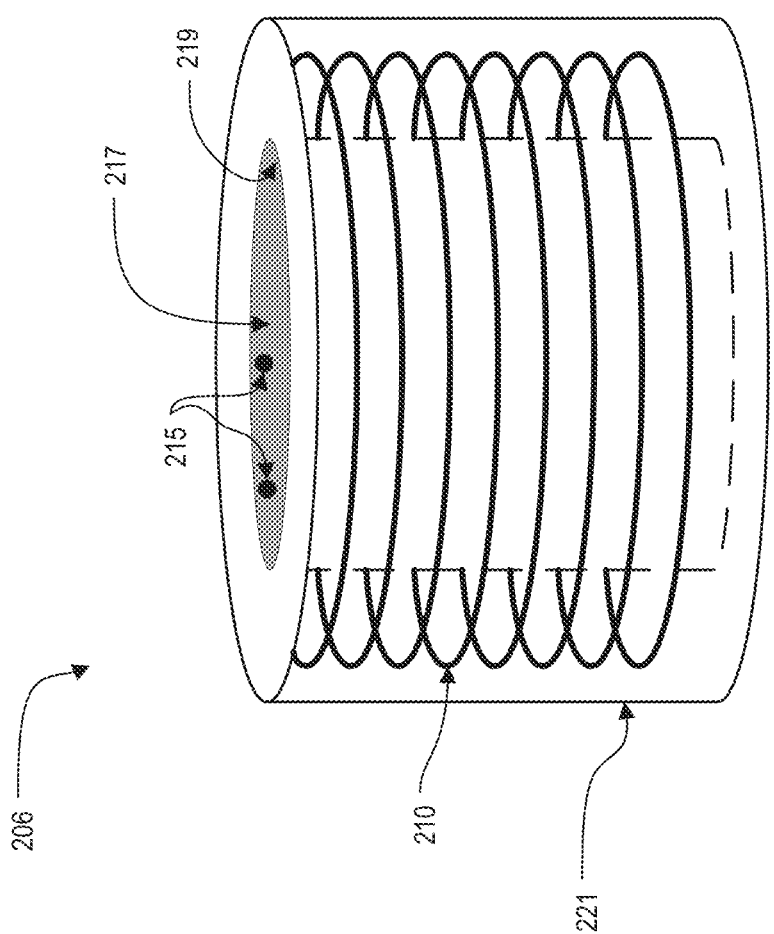
FIG. 2 is an example housing including an integrated antenna in accordance with an embodiment of the disclosure.

FIG. 2 is an example housing 206 including an integrated antenna in accordance with an embodiment of the present disclosure. The housing 206 may be one example of the housing 106. The illustrated embodiment of the housing 206 includes an outer surface 221, an inner surface 219, an antenna 210, and connection pads 215.

The housing 206 may be annular shaped with the inner surface 219 forming an inner diameter, and the outer surface 221 forming the outer diameter. The housing may have a finite thickness between the inner and outer surfaces 219 and 221, respectively, that provide a volume of material for integration of the antenna 210. The inner surface 219 may define an internal cavity 217 of the housing 206. The internal cavity 217 may provide a volume of space for disposing electronics and wiring, for example. In some embodiments, electronics disposed in the internal cavity 217 may be electrically coupled to the antenna 210 via one or more connection pads 215. In some embodiments, the outer diameter of the housing 206 may be up to 1.5 centimeters, and a length of the housing 206 may be from 0.5 mm to 10 mm.

The antenna 210 may be imbedded in a sidewall of the housing 206, and may be coupled to the connection pads 215. The antenna 210 may form a coil surrounding the internal cavity 217. By imbedding the antenna 210 into the sidewall of the housing 206, the overall diameter of the housing 206 may be limited to a minimum. Additionally, by imbedding the antenna 210 into the sidewall of the housing 206, an implantable device that includes the housing 206 may be more easily implanted over current devices, which may allow for less invasive implant procedures.

Figure 3:
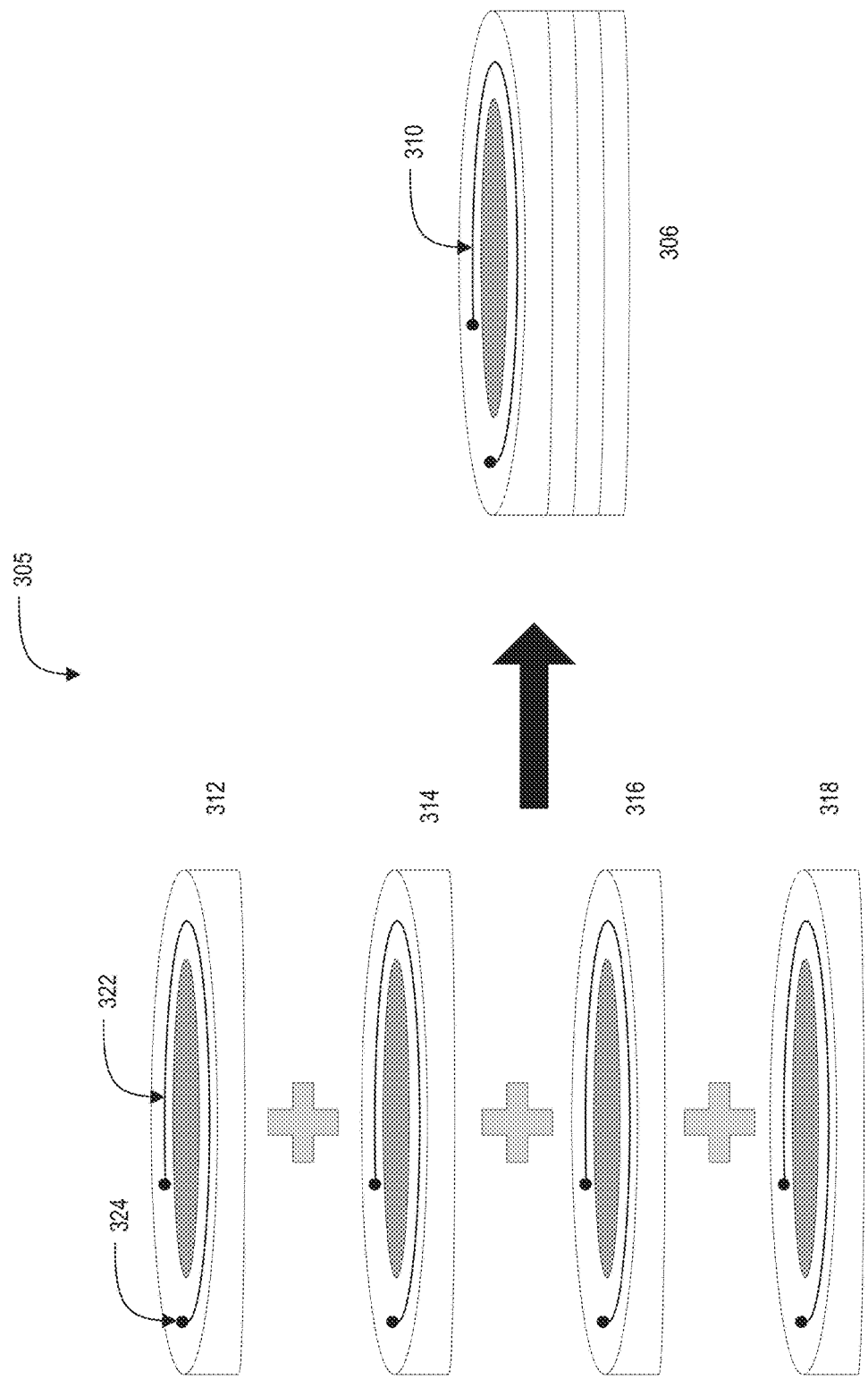
FIG. 3 is an example process for forming a housing with an integrated antenna in accordance with an embodiment of the present disclosure.

FIG. 3 is an example process 305 for forming a housing 306 with an integrated antenna 310 in accordance with an embodiment of the present disclosure. The process 305 may be one example process for forming the housing 306 with an integrated antenna. The housing 306 may be an example of the housings 106 and/or 206. In general, the process 305 may begin with a plurality of partially processed ceramic sheets that each include a portion of an integrated antenna loop disposed on at least one surface. Further, the partially processed sheets, which may also be referred to as green sheets, may be formed into a stack with respective end points of the integrated antenna aligned. The formed stack may subsequently be sintered to complete the processing and fully form the housing 306 with the integrated antenna 310.

The illustrated embodiment of the process 305 may begin with the green sheets 312 through 318. While only four green sheets are shown, the process 305 may include any number of green sheets, and the number of green sheets is a non-limiting aspect of the present disclosure. Each green sheet 312-318 may be formed from a ceramic, such as alumina, and have a partial conductive loop 322 disposed on at least one surface. In some embodiments, the partial conductive loops 322 may be screen printed onto each of the green sheets 312-318. Each partial conductive loop 322 may terminate at coupling nodes 324, which may be used to couple the partial conductive loops 322 of each of the adjacent green sheets 312-318 when formed into a stack. At least one coupled node 324 may be formed in a via that electrically couples the two sides of each of the green sheets 312-318. In some embodiments, the partial conductive loop 322 of each green sheet 312-318 along with the coupling nodes 324 may be formed from platinum. With regards to size, each of the green sheets 312-318 may be from 10 to 100 microns in thickness, and have any inner and outer radii as desired.

The plurality of green sheets 312-318 may be stacked one on the other with their respective coupling nodes 324 aligned to adjacent green sheets 312-318. Once the stack is formed, one or more sintering steps may be performed to complete processing the ceramic and to form the housing 306, as shown in the right side of FIG. 3. While lines are shown on the housing 306, the lines are included in FIG. 3 to illustrate the discrete green sheets. However, subsequent to the sintering step, the discrete green sheets may not be discernable due to the sintering causing the green sheets to form into a single housing 306. In some embodiments, the sintering process may be referred to as a platinum co-fire process that combines the platinum of the conductive elements with the ceramic of the green sheets 312-318.

Additionally, ferromagnetic layers may be incorporated into the green sheets 312-318 to in order to improve electromagnetic isolation, and improve the performance of the antenna. For example, the ferromagnetic layers may be formed on an inner surface of each of the green sheets 312-318 to isolate electronics disposed therein from the antenna. Alternatively, the ferromagnetic layers may be incorporated between the individual green sheets 312-318.

Figure 4A:
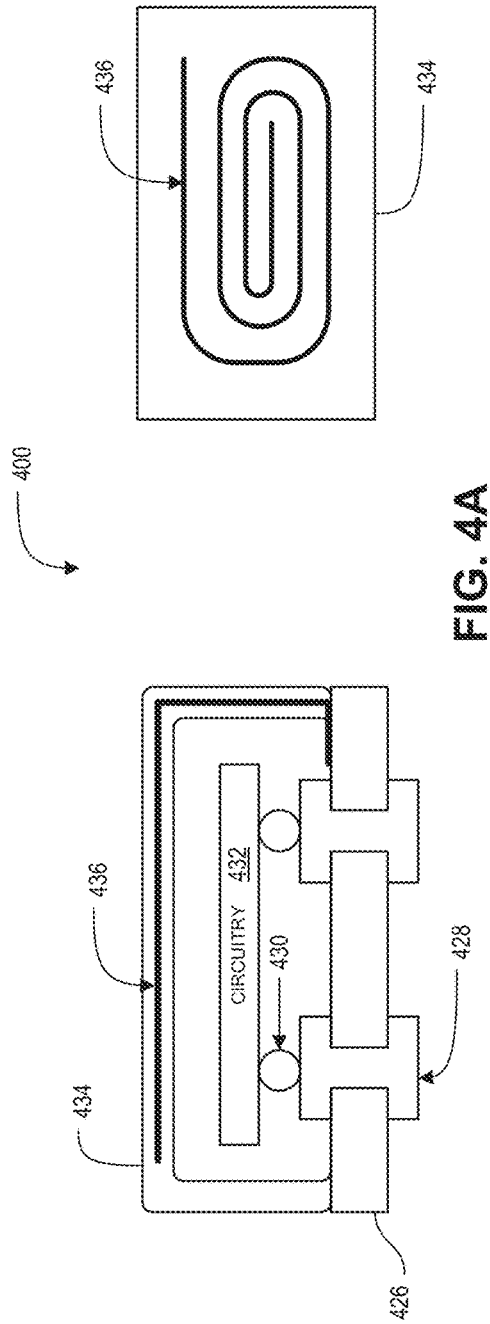
FIGS. 4A and 4B are ceramic housings including integrated inductors in accordance with an embodiment of the disclosure.

FIG. 4A is a cross-sectional view of an implantable device 400 including an integrated antenna in accordance with an embodiment of the present disclosure. The implantable device 400 may be an implantable device formed from one or more biocompatible ceramics and/or metals. The implantable device 400 may be similar to the implantable device 100 except for a change in form factor. The illustrated embodiment of the implantable device 400 includes a substrate 426, one or more feedthroughs 428, one or more ball bonds 430, circuitry 432, a housing 434, and an integrated antenna 436.

The substrate 426 and the housing 434 may both be formed from ceramic, such as alumina, and the antenna 436 may be integrated, e.g., imbedded, into the housing 434 during formation of the housing 434. For example, the housing 434 may be built by sintering together a plurality of ceramic green sheets that include formations of metal that form the housing 434 including the integrated antenna. The antenna 436 may be formed form a conductive material, such a platinum. The process 305 may be used to form the substrate 426 and the housing 434, but the green sheets would be shaped and stacked differently.

Referring to the left side of FIG. 4A, the circuitry 432 may be enclosed in the housing 434 and electrically coupled to the one or more ball bonds 430, which are electrically coupled to the one or more feedthroughs 428. Additionally, the circuitry 432 is coupled to the antenna 436 either via one of the ball bonds 430, or by a separate electrical coupling (not shown). While a battery is not shown in the implantable device 400, a battery or power source may be included in the circuitry 432, which may be charged via inductive coupling using the antenna 436. The antenna 436 may additionally provide data telemetry for the implantable device 400. The one or more feedthroughs 428 may be formed from a biocompatible metal and may form a hermetic seal with the surrounding substrate 426.

Figure 4B:
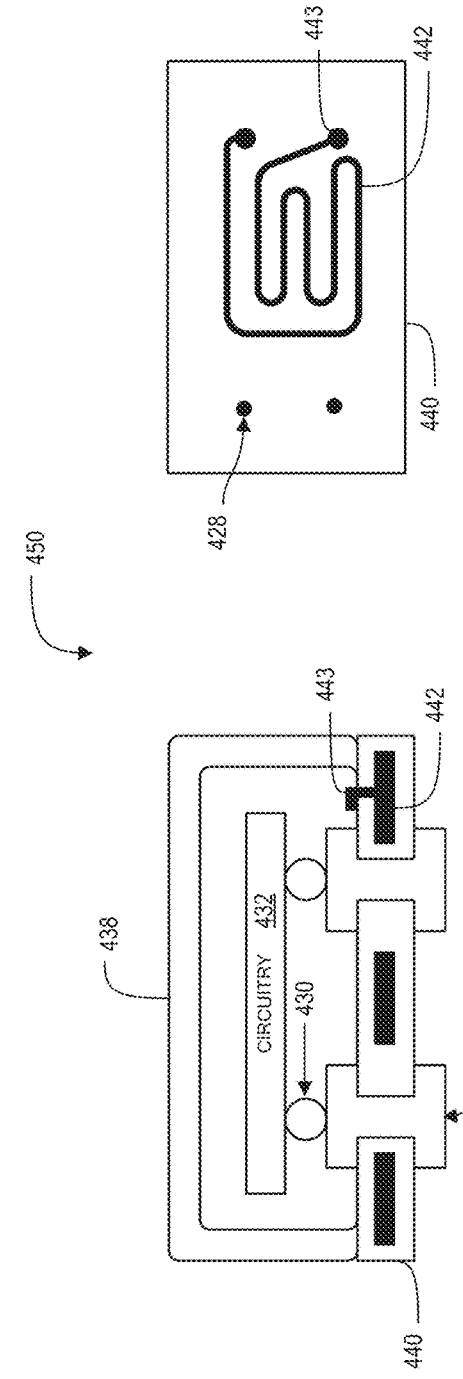

Referring to the right side of FIG. 4A, a plan view of the housing 434 including the integrated antenna 436 is shown. The integrated antenna 436 may be formed into a spiral, but other shapes are also contemplated, FIG. 4B is a cross-sectional view of an implantable device 450 including an integrated antenna in accordance with an embodiment of the present disclosure. The implantable device 450 may be substantially similar to the implantable device 400 except the antenna 442 is integrated into the substrate 440 instead of the housing 438. The illustrated embodiment of the implantable device 450 includes the substrate 440, one or more feedthroughs 428, one or more ball bonds 430, circuitry 432, antenna 442, coupling 443, and a housing 438. For sake of brevity, components of the implantable device 450 that are similar to like components of the implantable device 400 will not be discussed in detail with respect to FIG. 4B.

The substrate 440 may be formed from a plurality of green sheets that include the antenna 442, or at least portions thereof, and the one or more feedthroughs 428. The interface between the substrate 440 and the one or more feedthroughs 428 may form a hermetic seal, for example. The coupling 443 may be one or more conductive nodes for coupling the circuitry 432 to the antenna 442, and may be accessible from at least one side of the substrate 440.

Referring to the right side of the substrate 440, the feedthroughs 428 may be formed on one side to provide electrical coupling between the circuitry 432 and external electrodes, for example. Additionally, the antenna 442 may be laid out in any pattern that provides for transmission and receipt of electromagnetic signals, and the couplings 443 may be connections to the antenna 442 via partial vias.

Figure 5:
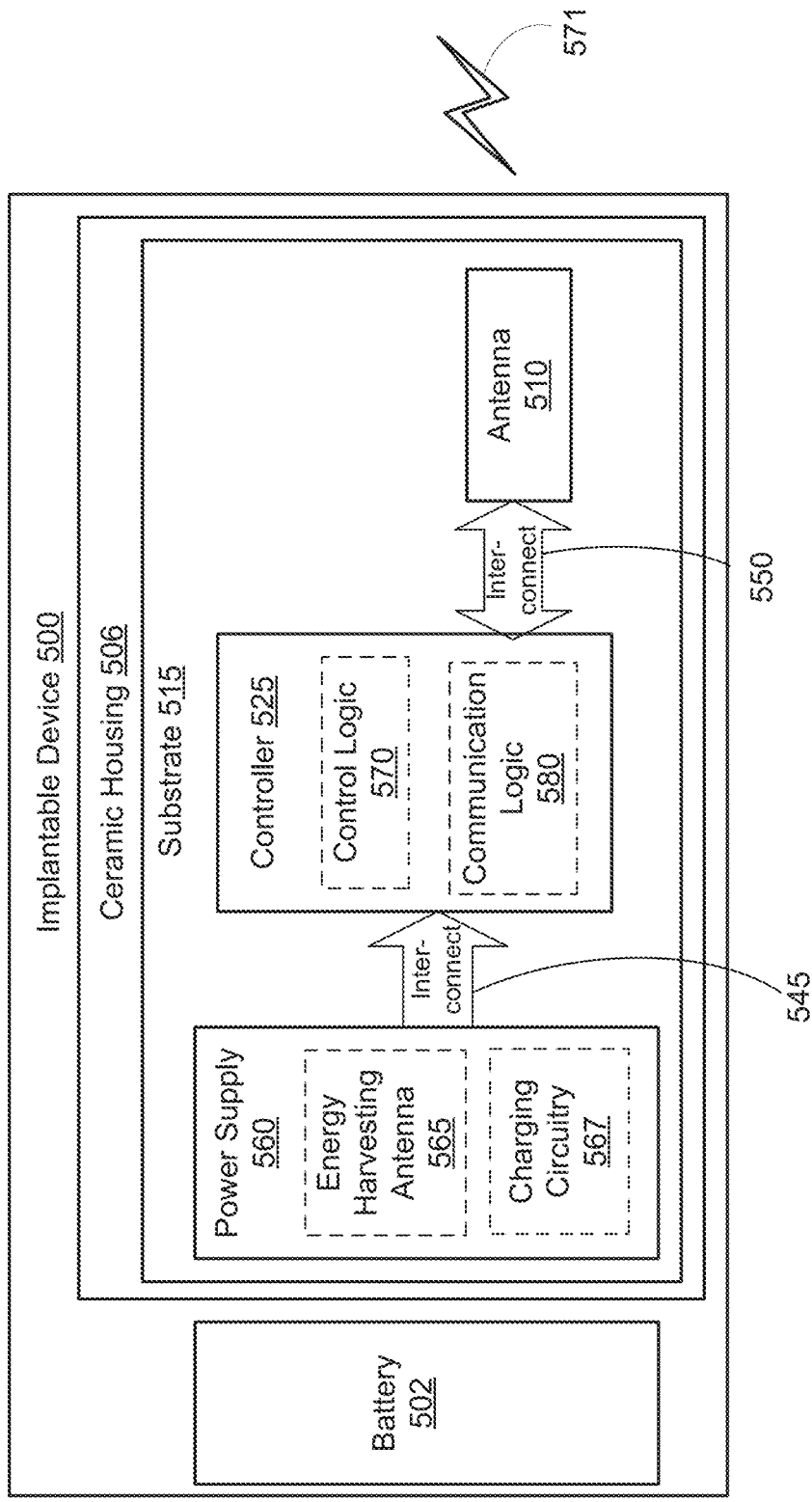
FIG. 5 is a functional block diagram of an implantable device 500 including an integrated antenna in accordance with an embodiment of the present disclosure.

FIG. 5 is a functional block diagram of an implantable device 500 including an integrated antenna in accordance with an embodiment of the present disclosure. Implantable device 500 may be an implantable device that requires at least one antenna for power and/or data telemetry. Example implantable devices include pacemakers, cochlear implants, and deep brain stimulators. In the depicted embodiment, implantable device 500 includes a ceramic housing 506, a battery 502, and a substrate 515 disposed within or surrounded by ceramic housing 506. The substrate 515 may provide a mounting surface for a power supply 560, a controller 525, and various interconnects 445 and 450. The substrate 515 and the associated electronics may be one implementation of the circuitry 111 and/or 432. The illustrated embodiment of power supply 560 includes an energy harvesting antenna 565, and charging circuitry 567. The power supply 560 may additionally be coupled to the battery 502. The illustrated embodiment of controller 525 includes control logic 570, and communication logic 580. As shown, battery 502 is disposed outside of the ceramic housing 506, but may alternatively be included within the ceramic housing 506.

Power supply 560 supplies operating voltages to the controller 525. Antenna 510 is operated by the controller 525 to communicate information to and/or from implantable device 500.

Substrate 515 includes one or more surfaces suitable for mounting controller 525, and power supply 520. Substrate 515 can be employed both as a mounting platform for chip-based circuitry (e.g., by flip-chip mounting) and/or as a platform for patterning conductive materials (e.g., gold, platinum, palladium, titanium, copper, aluminum, silver, metals, other conductive materials, combinations of these, etc.) to create electrodes, interconnects, antennae, etc. In some embodiments, interconnects 545 and 550 can be formed by depositing suitable patterns of conductive materials on substrate 515. A combination of resists, masks, and deposition techniques can be employed to pattern materials on substrate 515. Substrate 515 can be a relatively rigid material, such as polyethylene terephthalate ("PET") or another material sufficient to structurally support the circuitry and/or electronics within ceramic housing 506. Implantable device 500 can alternatively be arranged with a group of unconnected substrates rather than a single substrate 515. For example, controller 525 and power supply 560 can be mounted to separate substrates 515, and the two can be electrically connected via interconnects. Substrate 515 may also be a continuous piece of semiconductor, housing all or some of the aforementioned pieces of device architecture as integrated circuitry.

In the illustrated embodiment, power supply 560 is coupled to the battery 502 to power the various embedded electronics, including controller 525. Battery 502 may be inductively charged by charging circuitry 567 and energy harvesting antenna 565. In one embodiment, antenna 510 and energy harvesting antenna 565 are independent antennae, which serve their respective functions of energy harvesting and communications. In another embodiment, energy harvesting antenna 565 and antenna 510 are the same physical antenna that are time shared for their respective functions of inductive charging and wireless communications. Additionally, an inertial power scavenging system can be included to capture energy from ambient vibrations.

Charging circuitry 567 may include a rectifier/regulator to condition the captured energy for charging battery 502 or to directly power controller 525 without battery 502. Charging circuitry 567 may also include one or more energy storage devices to mitigate high frequency variations in energy harvesting antenna 565. For example, one or more energy storage devices (e.g., a capacitor, an inductor, etc.) can be connected to function as a low-pass filter.

Controller 525 contains logic to choreograph the operation of the other embedded components. Control logic 470 controls the general operation of implantable device 500, including providing a logical user interface, power control functionality, etc. Communication logic 580 provides communication protocols for wireless communication with one or more external readers via antenna 510. In one embodiment, communication logic 580 provides backscatter communication via antenna 510 when in the presence of an electromagnetic field 571 output from a reader. In one embodiment, communication logic 580 operates as a smart wireless radio-frequency identification ("RFID") tag that modulates the impedance of antenna 510 for backscatter wireless communications. The various logic modules of controller 525 may be implemented in software/firmware executed on a general purpose microprocessor, in hardware (e.g., application specific integrated circuit), or a combination of both.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An implantable device, comprising:
a cylindrical housing having a sidewall and an internal cavity, wherein the sidewall is formed from a ceramic, wherein an antenna is integrated into and embedded within the sidewall, and wherein the antenna forms a coil within the sidewall around the internal cavity;
a metallic feedthrough joined to a first end of the cylindrical housing;
a metallic collar joined to a second end of the cylindrical housing, the second end opposite the first end; and
a battery joined to the metallic collar.

2. The implantable device of claim 1, further comprising: control circuitry disposed within an inner cavity of the cylindrical housing and electrically coupled to the antenna.

3. The implantable device of claim 1, wherein the antenna is imbedded into the ceramic.

4. The implantable device of claim 1, wherein the cylindrical housing comprises a plurality of ceramic sheets stacked on top of each other with partial conductive loops disposed between stacked layers of the ceramic sheets, wherein the partial conductive loops collectively form the antenna.

5. The implantable device of claim 4, wherein a first end of a first partial conductive loop disposed at a first stacked layer is aligned with a second end of a second partial conductive loop disposed at a second stacked layer, different from but adjacent to the first stacked layer.

6. The implantable device of claim 1, wherein the metallic feedthrough provides connections between circuitry disposed within an inner cavity of the cylindrical housing and one or more external electrodes.

7. The implantable device of claim 1, wherein the battery is electrically coupled to circuitry disposed within an inner cavity of the cylindrical housing.

8. The implantable device of claim 1, wherein the metallic feedthrough and the metallic collar are joined to the cylindrical housing by brazing.

9. The implantable device of claim 1, wherein the battery is joined to the metallic collar by laser welding.

10. The implantable device of claim 1, wherein the ceramic is alumina or zirconia.

11. The implantable device of claim 1, wherein the antenna is formed from platinum or gold.

12. The implantable device of claim 1, further comprising a parallel plate capacitor integrated into the sidewall and electrically coupled to the antenna.

13. The implantable device of claim 1, further comprising a ferromagnetic material disposed on a surface of the internal cavity, wherein the ferromagnetic material provides electromagnetic isolation between the antenna and electronics disposed within the internal cavity.

14. The implantable device of claim 5, further comprising a conductive via disposed through a first one of the ceramic sheets, the conductive via electrically coupling the first partial conductive loop to the second partial conductive loop.

15. The implantable device of claim 4, wherein the stacked layers of the ceramic sheets comprise a sintered stack of ceramic sheets with the antenna embedded therein.

16. The implantable device of claim 1, wherein the metallic collar is disposed between the battery and the cylindrical housing and attaches the battery to the cylindrical housing.

17. An implantable device, comprising:
- a cylindrical housing having a sidewall and an internal cavity, and formed from a ceramic, wherein one or more passive electrical components are integrated into and embedded within the sidewall;
- a metallic feedthrough joined to a first end of the cylindrical housing;
- a metallic collar joined to a second end of the cylindrical housing, the second end opposite the first end; and
- a battery joined to the metallic collar.

18. The implantable device of claim 17, wherein the one or more passive electrical components at least includes a coil for inductive power transfer.

19. The implantable device of claim 17, wherein the one or more passive electrical components is an antenna coupled for power telemetry.

20. The implantable device of claim 17, wherein the one or more passive electrical components at least includes a parallel plate capacitor.

21. The implantable device of claim 17, wherein the one or more passive electrical components at least includes an inductor.

22. The implantable device of claim 17, further comprising:
- circuitry disposed within the internal cavity, wherein the one or more passive electrical components are electrically coupled to the circuitry.

* * * * *